US012726481B2

(12) United States Patent
Gelati et al.

(10) Patent No.: US 12,726,481 B2
(45) Date of Patent: Sep. 1, 2026

(54) CONNECTING DISPARATE, LARGE SCALE MEDICAL PRODUCTS, AND SERVICES TO A SINGLE ECOSYSTEM: A MODEL FOR IMPROVING INTRAOPERABILITY AND INTEROPERABILITY

(71) Applicant: Siemens Healthineers International AG, Steinhausen (CH)

(72) Inventors: Gionata Gelati, Rütihof AG (CH); Joakim Pyyry, Helsinki (FI); Kevin Anthony, Arvada, CO (US); Benjamin Moga, Soquel, CA (US); Christopher Smith, Dublin (IE)

(73) Assignee: Siemens Healthineers International AG, Steinhausen (CH)

( * ) Notice: Subject to any disclaimer, the term of this patent is extended or adjusted under 35 U.S.C. 154(b) by 120 days.

(21) Appl. No.: 18/424,300

(22) Filed: Jan. 26, 2024

(65) Prior Publication Data

US 2025/0247392 A1 Jul. 31, 2025

(51) Int. Cl.
*H04L 9/40* (2022.01)
*G16H 20/40* (2018.01)

(52) U.S. Cl.
CPC ........... *H04L 63/101* (2013.01); *G16H 20/40* (2018.01); *H04L 63/0807* (2013.01)

(58) Field of Classification Search
CPC ... H04L 63/0807; H04L 63/101; G16H 40/60; G16H 30/20
See application file for complete search history.

(56) References Cited

U.S. PATENT DOCUMENTS 11,899,824 B1 * 2/2024 Hall .................... G06F 21/6227
2008/0046292 A1 * 2/2008 Myers .................. G06F 16/283 705/3

(Continued)

FOREIGN PATENT DOCUMENTS

WO WO-2021257664 A1 * 12/2021 ......... H04L 63/0442

OTHER PUBLICATIONS

Britta Voss et al: "Interoperability of real-time public safety data: challenges and possible future states NIST IR 8255", NIST, National Institute of Standards and Technology (NIST), Jun. 19, 2019 (Jun. 19, 2019), pp. 1-90, XP061056245, DOI: 10.6028/NIST.IR.8255 Retrieved from the Internet: URL:https://nvlpubs.nist.gov/nistpubs/ir/2019/NIST.IR.8255.pdf [retrieved on Jun. 30, 2019].

(Continued)

*Primary Examiner* — Hee Soo Kim
(74) *Attorney, Agent, or Firm* — Foley & Lardner LLP

(57) ABSTRACT

Embodiments disclose herein implement a computing system in a computing network with hardware and software components of clinical system resources. The computing network may be a closed, private network. The clinical system resources may be situated on-premises or otherwise geographically proximate to the clinical installation (e.g., hospital, healthcare clinic). The clinical system resources may be heterogenous resources. The clinical system resources may access or execute interface programs (e.g., APIs) for performing interoperability operations on input data or instructions from the clinic database or upstream clinical system resource of the clinical networked computing system. For instance, the interface program may, for example, translate the data format of instructions or application data, or authenticate an upstream clinical system resource that sent the application data or instructions, among others. In an onboarding process, the integration program (Continued)

200

Receive onboard request for clinical system resource to access closed computing network 202

Perform authentication operation for authenticating the clinical system resource 204

Perform testing and verification operations for verifying the clinical system resource is an interoperable resource according to interface programs used by the clinical system resource 206

Perform validation operation for validating license data associated with the clinical system resource 208

Grant access rights to the clinical system resource based on validating, authenticating, and verifying the clinical system source 210

Store a set of resource configurations into a database record that represents a verified version of the clinical system resource 212

Optionally, revoke the access rights of the clinical system resource 214 may perform operations for authentication, license validation, and testing and verifying interoperability of the clinical system resource.

20 Claims, 3 Drawing Sheets

(56) References Cited

U.S. PATENT DOCUMENTS

| | | | | |
|---|---|---|---|---|
| 2013/0297973 | A1* | 11/2013 | Hyland | G16H 10/60 714/27 |
| 2015/0006612 | A1* | 1/2015 | Natoli | H04L 67/12 709/202 |

OTHER PUBLICATIONS

Extended European Search Report dated Jul. 2, 2025 on EPO App. 25153544.9-1122 (10 pages).

* cited by examiner

CONNECTING DISPARATE, LARGE SCALE MEDICAL PRODUCTS, AND SERVICES TO A SINGLE ECOSYSTEM: A MODEL FOR IMPROVING INTRAOPERABILITY AND INTEROPERABILITY

TECHNICAL FIELD

This application is generally related to interoperability and compatibility amongst heterogenous computing resources in a computing network. In particular, systems and methods for managing interoperability of data and services between various healthcare software applications and medical devices.

BACKGROUND

The market for radiation oncology products is filled with hardware and software products designed to assist and enhance provider-delivered treatment to patients. Currently, there is no unified platform or program to integrate these products (either hardware or software products) with a focus on improved clinical workflow, patient safety, regulatory compliance, and cybersecurity. A common technological hurdle for such integrations is resolving how to allow third party applications to become part of the integrated platform, while still preserving or persisting secure identification of the various different applications and governance of which application uses which resource of the platform (e.g., APIs, software services, data sources).

SUMMARY

Disclosed herein are systems and methods for addressing shortcomings in the art and may provide any number of additional or alternative benefits. Embodiments include a clinical computing system for radiotherapy planning and treatment, or other clinical or healthcare related therapy and treatment activities. A clinical computing system include in a closed, private computing network with hardware and software components of the clinical system resources situated on-premises or otherwise geographically proximate to the clinical installation (e.g., hospital, healthcare clinic). The clinical system resources may access or execute interface programs (e.g., APIs) for performing certain interoperability operations on input data or instructions from the clinic database or upstream clinical system resource of the clinical networked computing system. For instance, the interface program may, for example, translate the data format of instructions or application data, or authenticate an upstream clinical system resource that sent the application data or instructions, among others. In an onboarding process, the integration program may perform operations for authentication, license validation, and testing and verifying interoperability of the clinical system resource.

Embodiments may include a computer-method for hosting resources in a computing network. The method comprises obtaining, by a computer of a computing network, authentication information associated with a clinical system resource of the computing network. The authentication information includes a purported authentication data and an authentication protocol. The clinical system resource generates at least one attribute of a patient treatment. The method comprises authenticating, by the computer, the clinical system resource based upon comparing the purported authentication credential against a stored expected authentication credential. The method comprises identifying, by the computer, one or more interface programs for the clinical system resource to exchange the at least one attribute of the patient treatment with a software application of a clinical therapy machine. The method comprises verifying, by the computer, the clinical system resource as an interoperable resource in response to determining that the clinical system resource satisfies one or more interoperability testing thresholds corresponding to one or more interoperability testing operations using the one or more interface programs. The method comprises storing, by the computer, a set of resource configurations into a database record representing a verified version of the clinical system resource. The set of resource configurations includes a listing of function outputs, the authentication protocol, and a listing of the one or more interface programs for the clinical system resource. The resources may be heterogenous resources. The computing network may be a closed network having on-premises resources. The resources may be on-premises resources in a closed computing network. The closed computing network may include one or more computing devices, including the computer.

The patient treatment may include a radiotherapy treatment. The at least one attribute of the patient treatment includes an attribute of the patient radiotherapy treatment. The software application of the clinical therapy machine may include a patient radiotherapy machine.

The method may include obtaining, by a computer, purported license data associated with the clinical system resource; and validating, by the computer, the clinical system resource based upon comparing the purported license data against stored expected license data.

The method may include granting, by the computer, access rights to the clinical system resource for executing the one or more interface programs based upon authenticating, verifying, and validating the clinical system resource.

The method may include transmitting, by the computer, a security token to the clinical system resource indicating the access rights as granted to the clinical system resource.

The method may include generating, by the computer, a notification for an end-user device indicating a new version of the clinical system resource, in response to identifying a change to at least one the listing of functions or the authentication protocol compared against the verified version of the clinical system resource.

The method may include revoking, by the computer, access rights as granted to the clinical system resource for executing the one or more interface programs, in response to identifying a new version of the clinical system resource based upon a change to at least one the listing of functions or the authentication protocol compared against the verified version of the clinical system resource.

The one or more interface programs include at least one of data exchange and integration application programming interface (API), a healthcare scripting API, a quality assurance (QA) API, a database access API, a Motion Management Interface (MMI), or a Varian Treatment Interface (VTI®).

Determining that the clinical system resource satisfies one or more interoperability testing thresholds may include executing, by the computer, an interoperability testing operation for an interface program to generate one or more testing outputs; and determining, by the computer, a testing discrepancy for comparison against an interoperability testing threshold, based upon comparing the one or more testing outputs against one or more expected outputs for the interoperability testing operation.

Embodiments may include a system for hosting resources in a computing network. The system may comprise a database of a computing network configured to store a plurality of database records for a plurality of verified versions of a plurality of clinical system resources. The system may comprise a server of the computing network comprising a processor and configured to: obtain authentication information associated with a clinical system resource of the computing network, the authentication information including a purported authentication credential and an authentication protocol, wherein the clinical system resource generates at least one attribute of a patient treatment; authenticate the clinical system resource based upon comparing the purported authentication credential against a stored expected authentication credential; identify one or more interface programs for the clinical system resource to exchange the at least one attribute of the patient treatment with a software application of a clinical therapy machine; verify the clinical system resource as an interoperable resource in response to determining that the clinical system resource satisfies one or more interoperability testing thresholds corresponding to one or more interoperability testing operations using the one or more interface programs; and store a set of resource configurations into a database record of the database representing a verified version of the clinical system resource, the set of resource configurations including a listing of function outputs, the authentication protocol, and a listing of the one or more interface programs for the clinical system resource. The resources may be heterogenous resources. The computing network may be a closed network having on-premises resources. The resources may be on-premises resources in a closed computing network. The closed computing network may include one or more computing devices, including the computer.

The patient treatment may include a radiotherapy treatment. The at least one attribute of the patient treatment may include an attribute of the radiotherapy treatment. The software application of the clinical therapy machine may include a patient radiotherapy machine.

The server may be further configured to obtain purported license data associated with the clinical system resource; and validate the clinical system resource based upon comparing the purported license data against stored expected license data.

The server may be further configured to grant access rights to the clinical system resource for executing the one or more interface programs based upon authenticating, verifying, and validating the clinical system resource.

The server may be further configured to transmit a security token to the clinical system resource indicating the access rights as granted to the clinical system resource.

The server may be further configured to generate a notification for an end-user device indicating a new version of the clinical system resource, in response to identifying a change to at least one the listing of functions or the authentication protocol compared against the verified version of the clinical system resource.

The server may be further configured to revoke access rights as granted to the clinical system resource for executing the one or more interface programs, in response to identifying a new version of the clinical system resource based upon a change to at least one the listing of functions or the authentication protocol compared against the verified version of the clinical system resource.

The one or more interface programs include at least one of data exchange and integration application programming interface (API), a healthcare scripting API, a quality assurance (QA) API, a database access API, a Motion Management Interface (MMI), or a Varian Treatment Interface (VTI®).

When determining that the clinical system resource satisfies one or more interoperability testing thresholds, the server may be configured to execute an interoperability testing operation for an interface program to generate one or more testing outputs; and determine a testing discrepancy for comparison against an interoperability testing threshold, based upon comparing the one or more testing outputs against one or more expected outputs for the interoperability testing operation.

Embodiments may include a non-transitory computer-readable medium of a computing network coupled to one or more processors of the computing network and containing executable instructions that, when executed by one or more processors, causes the one or more processors to: obtain authentication information associated with a clinical system resource of the closed computing network, the authentication information including a purported authentication credential and an authentication protocol, wherein the clinical system resource generates at least one attribute of a patient treatment; authenticate the clinical system resource based upon comparing the purported authentication credential against a stored expected authentication credential; identify one or more interface programs for the clinical system resource to exchange the at least one attribute of the patient treatment with a software application of a clinical therapy machine; verify the clinical system resource as an interoperable resource in response to determining that the clinical system resource satisfies one or more interoperability testing thresholds corresponding to one or more interoperability testing operations using the one or more interface programs; and store a set of resource configurations into a database record of a database representing a verified version of the clinical system resource, the set of resource configurations including a listing of function outputs, the authentication protocol, a listing of the one or more interface programs for the clinical system resource. The computing network includes resources. The resources may be heterogenous resources. The computing network may be a closed network having on-premises resources. The resources may be on-premises resources in the closed computing network.

The patient treatment may include a radiotherapy treatment. The at least one attribute of the patient treatment includes an attribute of the patient radiotherapy treatment. The software application of the clinical therapy machine may include a patient radiotherapy machine.

The executable instructions, when executed by the one or more processors, may further cause the one or more processors to obtain purported license data associated with the clinical system resource; and validate the clinical system resource based upon comparing the purported license data against stored expected license data.

The executable instructions, when executed by the one or more processors, may further cause the one or more processors to grant access rights to the clinical system resource for executing the one or more interface programs based upon authenticating, verifying, and validating the clinical system resource; and transmit a security token to the clinical system resource indicating the access rights as granted to the clinical system resource.

The executable instructions, when executed by the one or more processors, may further cause the one or more processors to revoke access rights as granted to the clinical system resource for executing the one or more interface programs, in response to identifying a new version of the clinical system resource based upon a change to at least one listing of functions or the authentication protocol compared against the verified version of the clinical system resource.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1A:
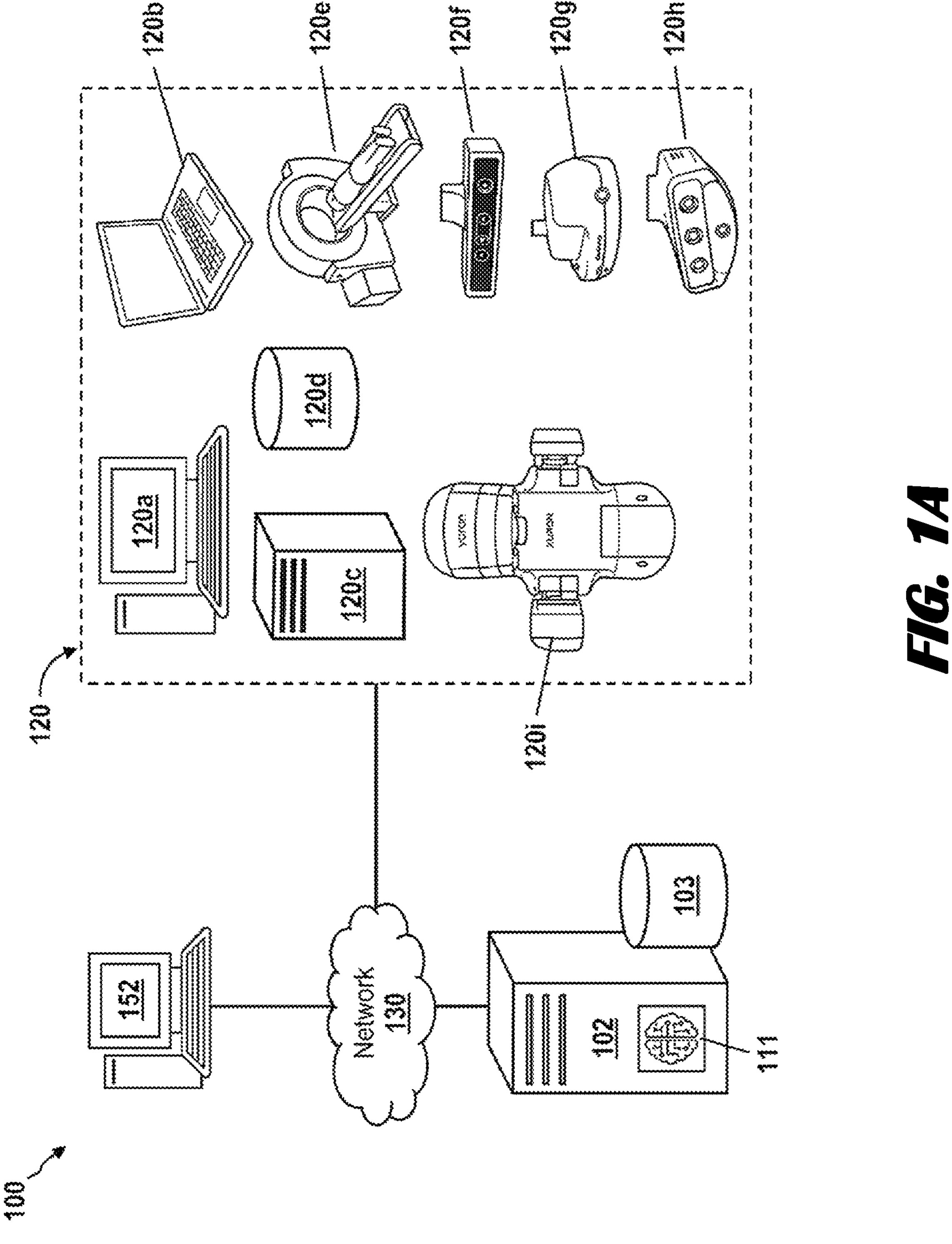
FIGS. 1A-1B illustrates components of a clinical network computing system that implements integration operations for interoperability and compatibility amongst hardware and software components of the clinical networked computing system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Computing network architectures deployed for radiation therapy or other clinical settings (e.g., hospitals, health clinics, physician offices, research laboratories) often include hardware and software products from a variety of vendors. The data generated from these products is circulated amongst the various products of the system for performing downstream operations. This requires clinical computing systems to employ various software programming, such as application programming interfaces (APIs), to identify or reconcile differences in data formats and software protocols in order to integrate each product into the ecosystem. The computing resources may be heterogenous, as hardware and software products or resources of different manufacturers or software developers, which typically require operations for analyzing and confirming interoperability, which includes data exchange between the products of different companies. For heterogenous resources, the embodiments described herein provide for processes for analyzing, confirming, and establishing interoperability amongst the various heterogenous products. The computing resources may be homogenous, as hardware and software products or resources of the same or related manufacturers or software developers. For homogeneous resources, the embodiments described herein provide for processes for analyzing, confirming, and establishing intraoperability amongst the various products. Although embodiments describe examples for "interoperability" analysis and confirmation operations, the embodiments may further include processes and functions for analyzing and confirming "intraoperability."

Although embodiments described herein mention clinical computing networks implemented for radiotherapy treatments and radiotherapy healthcare devices, embodiments are not so limited. Embodiment may include computing systems or networks implementing healthcare-related hardware (e.g., medical imaging devices, radiotherapy devices) and/or healthcare-related software components (e.g., healthcare hardware control software; treatment delivery software; treatment planning software).

A common approach for hosting a clinical computing ecosystem includes using a cloud or virtualized computing system. The various clinical or healthcare applications and application data are hosted in cloud-provisioned computing resources, allowing for functions such as storage, analytics, authentication, and data interoperability APIs to be hosted and executed in the provisioned resources of the cloud system. In a cloud system, each computing resource (e.g., hardware and software components, data storage locations) is referenced, called, or linked by accessing or calling uniform resource locators (URLs) as web-based pointers to the software or hardware components hosted in the cloud system via the Internet. The computing resources of these clinical systems typically require connectivity to access the hardware or software components associated with the URLs. Requiring Internet connectivity raises several problems, including degraded or lost connectivity to the cloud system resources, and exposure to Internet-based cyber exploits, among other potential problems.

Embodiments disclose herein implement a clinical computing system in a closed, private computing network with the hardware and software components situated on-premises or otherwise geographically proximate to the clinical installation (e.g., hospital, healthcare clinic). The software and hardware components of the clinical system (e.g., computing devices, sensors, medical devices (e.g., motion management devices, MRI devices), application servers, routers, switches) are housed within, or proximate to, the clinical installation. As such, the components do not require Internet-connectivity to function or access data related to patient care. The typical clinical computing systems do not implement on-premises computing resources; nor do typical clinical computing systems implement a closed-network computing architecture.

Clinical computing systems may include a heterogenous collection of hardware and software components with disparate data formats and authentication protocols, among other differences. Currently, there is no unified platform or program for integrating such heterogenous (hardware and software) products with a focus on the needs of a clinical environments, such as improved clinical workflow, patient safety, regulatory compliance, and cybersecurity, among others. A technological problem allowing disparate vendor products and applications to integrate into a common clinical computing system, while also preserving secure identification of the different applications and governing which applications may access which resources of the clinical system (e.g., APIs, application services, databases).

Vendors of the clinical system resources may address integration capabilities (e.g., interoperability and/or compatibility) across heterogenous components. In some cases, the interoperability capabilities of medical devices (e.g., motion management devices) are developed by the vendor that produced product, and then implemented and verified in a clinical network via software emulators, and finally validated by a clinical customer using the clinical network system. A problem is that interoperability across hardware devices is time-consuming and expensive, where the costs are distributed to the end-using clinical customer or patients.

Moreover, the integration of disparate software applications, including clinical system resources for Radiation Oncology solutions, has often been the responsibility of the clinical customer. The clinical customer typically worked with multiple vendor products to find a best-available solution for integration, coordinated parties and work tasks, implemented the integration, and provided long-term support of the integration. Although conventional healthcare-integration standards (e.g., Health Level Seven (HL7) standards, Digital Imaging and Communications in Medicine (DICOM) standard) have reduced and streamlined the amount of integration options, these conventional standards are merely data formatting standards, and cannot provide the foundations of a clinical computing system where new vendors and applications can be onboarded into the clinical computing system and can ultimately contribute to the ongoing clinical workflow of the hardware and software components.

Embodiments described herein implement a unified approach to integration that is consistent for hardware and software interoperability and/or compatibility. The clinical computing network systems described herein function as a unified clinical platform, which includes supporting processes, assures end-using clinicians that the integration developed between components has been certified as safe to use, regulatory compliant, and secure from unintended or unauthorized use.

Embodiments may include various interface programs (e.g., APIs) and standards-enforcing programs for healthcare software application interoperability and/or hardware compatibility. Non-limiting examples of the interfaces may include a data exchange and integration API ("data exchange API"), a healthcare scripting API, a quality assurance (QA) API, a database access API ("DB access API"), and Motion Management Interface (MMI), among others.

The data exchange API enables seamless data exchange and integration amongst the computing devices or clinical system resources of the clinical networked computing system. The data exchange API may support and perform, for example, Fast Healthcare Interoperability Resources (FHIR) standards or other standardized or proprietary protocols. The data exchange API, executed by the integration program or the clinical system resources, facilitates interoperability between the hardware or software clinical system resources.

The scripting API of the clinical networked computing system includes a software library and programming interface that, for example, accesses treatment planning information within a healthcare scripting application service (e.g., Eclipse®). In some implementations, the scripting API of the clinical networked computing system offers the same functionality as typical scripting API implementations and may further include an additional executable layer of identification and authorization tailored to be used by the hardware and software of the clinical system resources produced by various enterprise-level third-party vendor products.

The QA interface may simplify the integration processes for different QA objects and applicable data elements in the clinical networked computing system. When combining functionalities from various clinical system resources of the clinical networked computing system, the QA interface may be used to, for example, validate data quality, beneficially enhancing scalability, usability, and efficiency.

The DB access API enables the clinical system resource or the integration program to generate and issue SQL queries (e.g., select statements) to databases containing, for example, patient information or treatment information generated by software applications of the clinical networked computing system.

The MMI may translate and validate the motion and position data exchanged between the radiation treatment device and the treatment sensors (e.g., cameras) providing the patient's motion and posture information for adjusting the radiation treatment device. The treatment sensors may transmit various types of data related to the patient's position and motion to a control processor or computing device controlling the operations of the radiation treatment device, which may invoke or execute the MMI to ingest the motion and position information into a format compatible with the radiation treatment device.

Embodiments may include additional or alternative types of interfaces, such as an authentication API or a radiotherapy controller API. The authentication API allows computing devices of the clinical computing system to authenticate one another, which may include requesting an authentication status and presenting an authentication status. The controller API, such as a Virtual Treatment Interface (VTi®), allows certain computing resources to control and monitor the radiotherapy treatment machines. The controlling API facilitates the seamless integration of heterogenous computing resource, enabling the disparate computing devices and clinical therapy machines (e.g., radiotherapy machines, clinical imaging or scanning machines) to exchange data. Using the controlling API, the data related to patient positioning, beam control, and imaging can be shared across the heterogenous clinical system resources.

The interface programs (e.g., APIs) may correspond to functional domains of the clinical system resources. The functional domains represent functional or operational purposes of the clinical system resources. Non-limiting examples of the functional domains include practice management, treatment planning, quality assurance, motion management, and treatment delivery. The integration program and clinical system resources may implement interfaces and/or software applications corresponding to the functional domain(s).

The practice management domain includes clinical system resources for managing operations of the clinic. The practice management domain in radiation therapy refers to the administrative and managerial aspects of running a radiation therapy practice. This includes scheduling patient appointments, billing for services, managing patient records, ensuring compliance with regulatory standards, and coordinating care with other healthcare providers. The goal of practice management functions and features is to ensure that the practice operates smoothly and efficiently, providing high-quality care to patients while also maintaining financial sustainability.

The treatment planning domain in the context of radiation therapy (or other clinic computing systems) involves creating a detailed plan for the delivery of radiation doses to the patient's tumor site. This plan is designed to effectively target the cancer cells while minimizing exposure to surrounding healthy tissues. The treatment planning domain in radiation therapy may make use of API-based interoperability standards, such as HL7's FHIR standard. This allows for the rapid creation and deployment of different functions and facilitates the exchange of data between various clinical system resources involved in the treatment process, such as patient management, machine control, and electronic health records.

The QA domain in radiation therapy treatment systems (or other clinic computing systems) includes hardware and software functions intended to ensure the accuracy and reproducibility of treatment data outputs and treatment delivery. The QA domain may involve a range of checks and procedures designed to verify that aspects of the treatment domains, from treatment planning through to treatment delivery, are performed correctly and consistently.

The motion management domain in radiation therapy (or other clinic computing systems) includes hardware and software functions for mitigating the effects of a patient's intra-fraction respiratory motion and position during treatment, particularly for lung and upper abdominal tumors. The motion management domain involves, for example, measuring, monitoring, and managing the patient's respiratory motion to ensure accurate treatment delivery. The motion management domain includes the MMI.

The treatment delivery domain in radiation therapy (or other clinic computing systems) includes hardware and software functions for the actual administration of the radiation treatment (e.g., controlling the radiation treatment device) to the patient as per the treatment plan. The treatment delivery domain involves complex machinery, such as radiation therapy machines, linear accelerators, medical imaging systems, and robotic arms, to deliver precise doses of radiation to the tumor site while sparing surrounding healthy tissue or provide other forms of care. The treatment delivery domain often incorporates real-time imaging and patient positioning systems to ensure accuracy. Interoperability in the treatment delivery domain might involve APIs for machine control, patient safety systems, and integration with other clinical systems. The goal of the treatment delivery domain is intended to deliver the treatment safely, effectively, and comfortably.

In many instances, the clinical system resource executing the interface program is the clinical system resource where the software application invoking the interface is installed and run. In the context of radiation therapy and interoperability (or other clinical systems), the computing resource executing the API can vary based on the specific use case. For instance, when the API is used for treatment planning, the API may be executed on a specialized treatment planning computer system. If the API is used for machine control, then the API might be executed on the radiation therapy machine's control system. If the API is for integrating with electronic health records, then the API may be executed on a client computing device (e.g., clinic computer, physician computer, clinic server, clinic database) where the electronic health records are accessed, generated, stored, or hosted. In some cases, a centralized integration server may invoke and implement the API on behalf of another clinical system resource of the clinical system.

Components of Example Systems

Figure 1B:
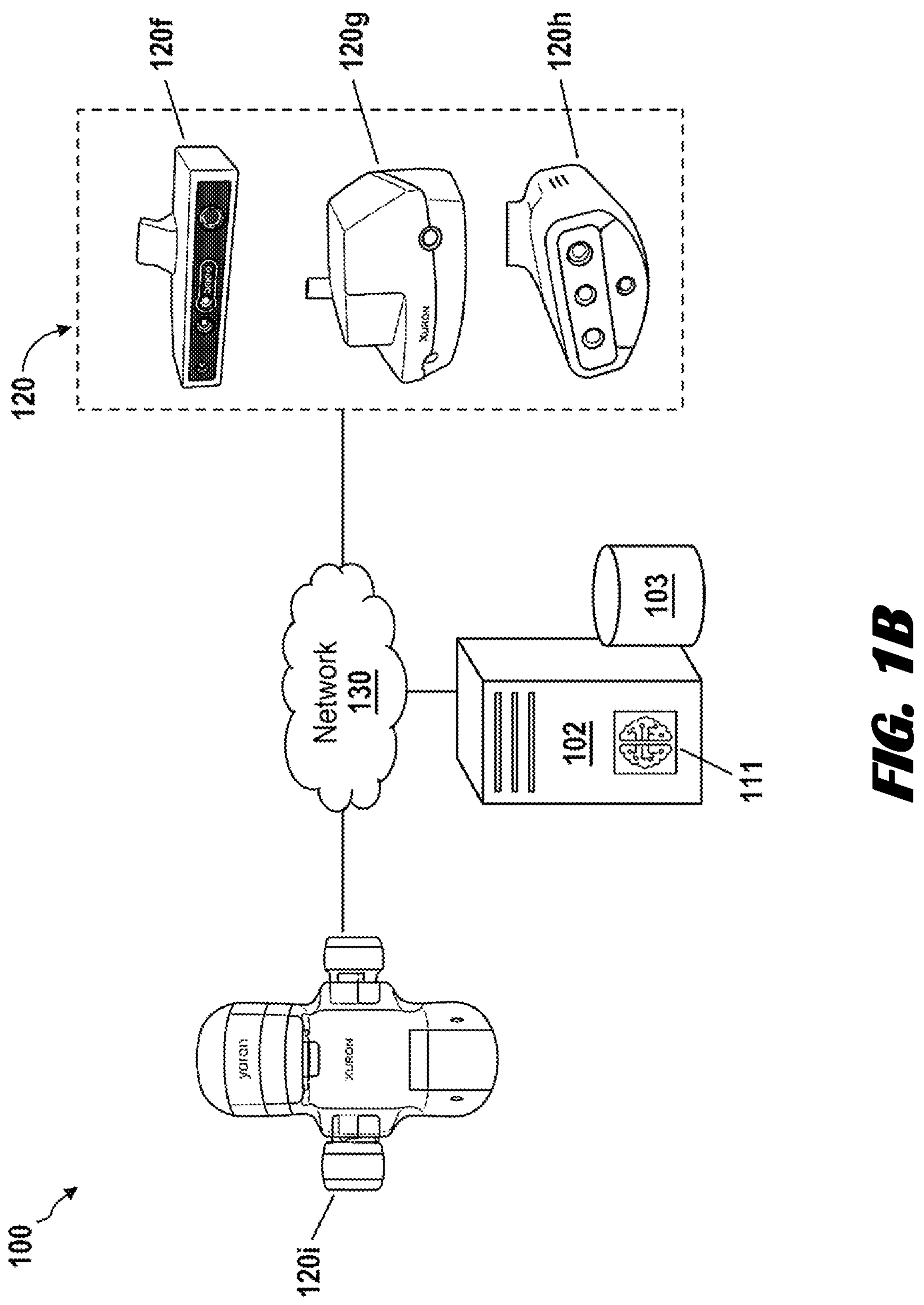

FIGS. 1A-1B illustrates components of a clinical network computing system 100 that implements integration operations for interoperability and compatibility amongst hardware and software components of the clinical networked computing system 100, according to an embodiment.

With reference to FIG. 1A, the clinical networked computing system 100 includes integration servers 102, clinical system resources 120*a*-120*i* (generally referred to herein as clinical system resources 120), and client devices 152. The various hardware and software components of the clinical networked computing system 100 communicate with one another via a closed network 130. The components of the clinical networked computing system 100, including the various computing devices or clinical system resources 120, and the components of the closed network 130 may be situated on-premises (e.g., situated in or proximate to a physical clinical installation). The clinical networked computing system 100 is not confined to the components described herein and may include additional or other components, not shown for brevity, which could be considered within the scope of the embodiments described herein.

The closed network 130 comprises various hardware and software components for handling device communications, including switches, routers, firewalls, proxy servers, and the like. The closed network 130 may employ wired and/or wireless communications according to one or more standards and/or via one or more transportation mediums. The communications over the closed network 130 may be performed in accordance with various communication protocols such as Transmission Control Protocol and Internet Protocol (TCP/IP), User Datagram Protocol (UDP), and IEEE communication protocols. In one example, the closed network 130 may include wireless communications according to Bluetooth or Wi-Fi specification sets or another standard or proprietary wireless communication protocol. Examples of the closed network 130 may include a private or public LAN, WLAN, CAN, and/or intranet, contained within a physical and logical network architecture of the clinical installation.

The clinical system resources 120 include various heterogenous hardware and software components (e.g., from disparate vendors or product lines; implement disparate data schemas or formats) for performing various tasks associated with radiotherapy treatment, or other forms of clinical patient care or administration. Non-limiting examples of the clinical system resources 120 include clinic computers 120*a*, physician devices 120*b*, clinic servers 120*c*, clinic databases 120*d*, medical imaging devices 120*e*, sensors 120*f*-120*h*, and a radiation treatment device 120*i*, among other types of hardware and software components of the clinical networked computing system 100.

The clinical system resources 120 include various clinic computing devices 120*a*-120*c*, including the clinic computers 120*a*, physician devices 120*b*, and/or clinic servers 120*c* may be computing devices comprising processors, non-transitory storage, and software programming for performing various processes and tasks described herein. The clinic computing devices 120*a*-120*c* may host or execute various software applications related to certain functional domains (e.g., treatment planning, treatment delivery). These software applications may ingest and analyze various types of data from the clinic database 120*d* or other data sources and generate various outputs including application data or executable instructions for one or more clinical system resources 120. The clinic computing devices 120*a*-120*c* may store the outputs into the clinic database 120*d*, and/or transmit the outputs to other clinical system resources 120 to perform downstream operations. The clinic computing devices 120*a*-120*c* may access or execute interface programs (e.g., APIs) for performing certain interoperability operations on input data or instructions from the clinic database 120*d* or upstream clinical system resource 120 of the clinical networked computing system 100. For instance, the interface program may, for example, translate the data format of instructions or application data, or authenticate an upstream clinical system resource 120 that sent the application data or instructions, among others.

The medical imaging device 120*e* includes hardware and software for generating medical image data for a patient. Non-limiting examples of the medical imaging device 120*e* include an MRI device, CAT device, and X-Ray device, among other types of medical imaging devices 120*e*. The medical imaging device 120*e* includes an integrated processing device and/or receives instructions from the clinic computing devices 120*a*-120*c*. The image data may be stored into the clinic database 120*d* into data records associated with the patient or the patient treatment. The medical imaging device 120*e* may access or execute interface programs (e.g., APIs) for performing certain interoperability operations on input data or instructions from the clinic database 120*d* or other clinical system resource 120 of the clinical networked computing system 100.

The radiation treatment device 120*i* includes hardware and software for performing radiation therapy treatments on patients. The radiation treatment device 120*i* may receive various inputs from other devices of the clinical networked computing system 100 such that a computing device (e.g., administrator computer 152, integrated processor of the radiation treatment device 120*i*) managing the radiation treatment device 120*i* may adjust the radiation treatment device 120*i* operations (e.g., beam angles, treatment attributes, radiation parameters) based on the instructions from the administrator computer 152 or in response to various data inputs received from the treatment sensors 120*f*-120*h*. For instance, the radiation treatment device 120*i* includes the radiation therapy machine that adjusts a gantry, beam-blocking device (e.g., multi-leaf collimator MLC), and couch based on optimized beam angles, where the optimized beam angle is an angle of the radiation treatment device 120*i* that emits radiation. The radiation treatment device 120*i* and/or the treatment sensors 120*f*-120*h* may access or execute interface programs (e.g., APIs) for performing certain interoperability operations on input data or instructions from other clinical system resource 120 of the clinical networked computing system 100.

An integration database 103 store various types of data about the clinical system resources 120 that the integration server 102 verified and certified as being integrated (e.g., interoperable, compatible) with the clinical networked computing system 100. The integration database 103 may be hosted by one or more computing devices of the clinical networked computing system 100 comprising hardware components (e.g., processors, non-transitory machine-readable storage) and software components (e.g., database management system) capable of performing the various processes and tasks described herein. The database records stored in the integration database 103 may represent verified versions of clinical system resource 120, which an integration program 111 of the integration server 102 verifies as being integrated (e.g., interoperable, compatible, both) with the clinical networked computing system 100. The database record for the verified version includes various types of information about the particular version or the clinical system resource 120. Non-limiting examples of the data stored in the integration database 103 include a list of functions, functional domains, data formats of inputs or outputs, and authentication protocols, among other types of information about the particular version or the clinical system resource 120.

An integration server 102 includes a computing device comprising hardware (e.g., CPU) and software components (e.g., integration program 111) capable of performing the various features and functions of the integration server 102 described herein. The integration server 102 executes an integration program 111 that performs various functions for managing integration (e.g., interoperability and compatibly) amongst the various clinical system resources 120 of the clinical networked computing system 100. Non-limiting examples of the integration functions performed by the integration program 111 include onboarding clinical system resources 120, authenticating clinical system resources 120, verifying clinical system resources 120, clinical system resources 120, and managing the interfaces for clinical system resources 120, among other possible integration functions. The integration program 111 performs the integration functions that unify or integrate the clinical system resources 120 (e.g., enterprise-level third-party vendor medical products and services in the clinical system resources 120) within the clinical networked computing system 100. The integration program 111 enhances interoperability amongst the clinical system resources 120, which may beneficially yield improved integration, workflows, user experiences, and patient outcomes. The integration program 111 may, for example, prioritize conformance, compliance, regulatory adherence, data privacy, and cybersecurity amongst the clinical system resources 120.

The integration program 111 may verify the interoperability of the new clinical system resource 120 and capture various types of information about the clinical system resource 120. The integration program 111 may store the information about the clinical system resource 120 into a database record of the integration database 103 representing a new instance of a verified version of the particular clinical system resource 120.

In many instances, the clinical system resources 120 implement the interface programs (e.g., APIs) for performing the integration operations. In some cases, however, the integration program 111 may implement the interface programs on behalf a clinical system resource 120, where the integration server 102 is an intermediate destination for a data exchange between clinical system resources 120 via the closed network 130.

The interface programs (e.g., APIs) may correspond to functional domains of the clinical system resources 120. The functional domains represent functional or operational purposes of the clinical system resources 120. Non-limiting examples of the functional domains include practice management, treatment planning, quality assurance, motion management, and treatment delivery. The integration program 111 and clinical system resources 120 may implement interfaces and/or software applications corresponding to the functional domain(s). In the context of radiation therapy and interoperability, the clinical system resource 120 executing the interface program may vary. In many instances, the clinical system resource 120 invoking and executing the interface program is the particular clinical system resource 120 where the software application using the interface is installed and run. As an example, when the clinical system resource 120 uses the interface program for treatment planning, the interface program may be invoked by a clinic computing device 120*a*-120*c* executing specialized software application for treatment planning. As another example, when the interface program is used for machine control, then the interface program might be executed by a control program of the radiation treatment device 120*i*. As another example, if the interface program is configured for integrating data exchanges of electronic health records, the interface program may be invoked and executed on the clinic computer 120*a*, clinic server 120*c*, or clinic database 120*d* where the electronic health records are hosted.

The interfaces may include a data exchange and integration API ("data API"). The data API enables seamless data exchange and integration amongst the computing devices or clinical system resources 120 of the clinical networked computing system 100. The data API may support and perform, for example, FHIR standards or other proprietary protocols. The data API, executed by the integration program 111 or the clinical system resources 120, facilitates interoperability between the hardware or software clinical system resources 120. For instance, the data API may convert or translate data formats to communicate data inputs and outputs amongst the clinical system resources 120.

The interfaces may include a scripting API, implemented by the clinical system resources 120 or the integration program 111. The scripting API of the clinical networked computing system 100 includes a software library and programming interface that, for example, accesses treatment planning information within a healthcare scripting application service (e.g., Eclipse®). In some implementations, the scripting API of the clinical networked computing system 100 offers the same functionality as typical scripting API implementations and may further include an additional executable layer of identification and authorization tailored to be used by the hardware and software of the clinical system resources 120 produced by various enterprise-level third-party vendor products. Some embodiments of the scripting API may be intended for heterogenous third-party vendor products, while some embodiments of the scripting API are designed for previously certified or vendor-specific products.

A QA API may be executed by the integration program 111 or the clinical system resources 120. The QA interface may simplify the integration processes for different QA objects in the clinical networked computing system 100. When combining functionalities from various clinical system resources 120 of the clinical networked computing system 100, the QA interface may be used to, for example, validate data quality, beneficially enhancing scalability, usability, and efficiency.

The MMI may translate and validate the motion and position data exchanged between the radiation treatment device 120*i* and the treatment sensors 120*f*-120*h* (e.g., cameras)). The treatment sensors 120*f*-120*h* may transmit various types of data related to a patient's position and motion to a control processor or computing device controlling the operations of the radiation treatment device 120*i*, which may invoke or execute the MMI to ingest the motion and position information into a format compatible with the radiation treatment device 120*i*.

The clinical system resources 120 (e.g., medical imaging device 120*e*, radiation treatment device 120*i*) and/or the integration program 111 may implement and apply the Digital Imaging and Communications in Medicine (DICOM) standard for communicating image data. In some cases, a DICOM Radiation Therapy (RT) interface specifies data structures or objects specifically designed for radiotherapy. The integration program 111 provides various communication interface operations amongst the various clinical system resources 120 of the clinical networked computing system 100. For instance, the data API may be an interface that implements the DICOM or DICOM RT standards for exchange data. In some embodiments, the integration program 111 or other component of the clinical networked computing system 100 implements an event subscription-publication framework. The integration server 102 may receive and "publish" an event as an input received from a clinical system resources 120. The integration server 102 implements a listener or subscription program that subscribes to events published to the event framework. In some cases, the events include DICOM events (according to the DICOM data standards) that the clinical system resources 120 or the integration program 111 publishes to the event framework.

In some cases, the interfaces include a DB access API that enables the clinical system resource 120 or the integration program 111 to generate and issue SQL queries (e.g., select statements) to the databases 120*d* containing, for example, patient information or treatment information generated by software applications of the clinical networked computing system 100.

The integration program 111 performs onboarding functions when an administrator or vendor introduces a new or updated (hardware or software) clinical system resource 120 into the clinical networked computing system 100. The onboarding functions may include, for example, authenticating the clinical system resource 120 as having privileges or access rights to access the closed network 130; verifying a license of the clinical system resource 120 granting permission for the clinical system resource 120 to access and invoke the interface programs and/or computing resources of the clinical networked computing system 100; and testing and validating the interoperability of the clinical system resource 120 and other computing resources of the clinical networked computing system 100, among other potential functions.

The integration program 111 may verify license data associated with the clinical system resources 120. The license data grants the clinical system resources 120 access to the clinical networked computing system 100, including the integration operations of the integration program 111. The integration program 111 authorizes the clinical system resource 120 based upon the license data and grants the clinical system resource 120 access to various functions of the integration program 111 or the clinical system resources 120, including the interface programs or events (e.g., DICOM events). During the onboarding process (or other integration process), the integration program 111 may obtain (e.g., retrieve, receive) a license input containing the license data from the clinical system resource clinical system resource 120. The integration program 111 may verify the purported license data of the clinical system resource 120 against prestored expected license data, which may be stored in the integration database 103 or in integration server 102 and accessible to the integration program 111.

As an example, during the onboarding process or at a login-time, the clinical system resource 120 may call a license verification interface and submit purported license data for the particular clinical system resource 120 to the integration program 111. The integration program 111 may execute (or instruct the integration server 102 to execute) the license verification operations for the clinical system resource 120, using the purported license data obtained from the clinical system resource 120. The license verification operation of the integration server 102 may, for example, compare the purported license data against prestored expected license data for the clinical system resource 120. If the integration server 102 successfully verifies the license of the clinical system resource 120, then the integration server 102 may grant the particular clinical system resource 120 a set of access privileges or rights to access other computing resources of the clinical networked computing system 100. During the onboarding process, the integration program 111 verifies that the clinical system resource 120 is a new verified version of the clinical system resource 120. In this way, in some cases the onboarding process may beneficially ensure that a developed commercial interface could be deployed and maintained for the clinical system resources 120 that have previously established interoperability as part of the clinical system 100.

In some implementations, an interface program includes instructions for the clinical system resource 120 to provide the license data, when the clinical system resource 120 invokes the particular interface program. The interface program may, for example, request the purported license data and confirm the purported license data against the stored expected license data (e.g., license key), which may be stored in the integration server 102 or integration database 103 (or another non-transitory storage medium of the clinical networked computing system 100).

The integration program 111 may execute authentication operations or implement interface programs that perform the authentication operations for authenticating the clinical system resources 120. For instance, the clinical system resource 120 or the integration program 111 may invoke the authentication operations and request authentication information from the clinical system resource 120. The authentication operations may be executed by another clinical system resource 120 or the integration server 102 (or any other computing device of the clinical networked computing system 100), using the purported authentication data received from the clinical system resource 120. The authentication operations may authenticate the access rights of the clinical system resource 120 and the particular access privileges to access particular resources of the clinical networked computing system 100. The authentication During the onboarding process for the clinical system resource 120, the integration program 111 may determine the authentication protocols implemented by the clinical system resource 120 and select a corresponding authentication interface based on the authentication protocol. The integration program 111 may store the authentication protocol information for the clinical system resource 120 into the verified version record of the integration database 103. Additionally or alternatively, the integration program 111 may store the authentication interface selected for the clinical system resource 120 into the verified version record of the integration database 103. The clinical system resource 120 may invoke the authentication operations of the integration server 102 or other component of the clinical networked computing system 100 by calling the authentication interface assigned by the integration program 111. The integration server 102 or other component of the clinical networked computing system 100 may execute the authentication functions according to the authentication protocols of the particular clinical system resource 120.

As an example, during the onboarding process or at a login-time, the clinical system resource 120 may call the authentication interface and submit purported authentication credentials for the particular clinical system resource 120 to the integration program 111. The integration program 111 may execute (or instruct the integration server 102 to execute) the authentication operations for the clinical system resource 120, using the purported authentication credentials obtained from the clinical system resource 120. The authentication operation of the integration server 102 may, for example, compare the purported authentication credentials against prestored expected credentials for the clinical system resource 120. If the integration server 102 successfully authenticates the clinical system resource 120, then the integration server 102 may grant the particular clinical system resource 120 a set of access privileges to access other computing resources of the clinical networked computing system 100. During the onboarding process, the integration program 111 authenticates the clinical system resource 120 as a new verified version of the clinical system resource 120.

In some embodiments, the authentication operations issue and reference security tokens stored at the clinical system resources 120 or other non-transitory storage medium. The authentication operations issue the security tokens to clinical system resources 120 to prove the clinical system resources 120 were previously authenticated. After successfully authenticating a particular clinical system resource 120, the integration server 102 (or other device of the clinical networked computing system 100) provides a security token to the authenticated clinical system resource 120. The other clinical system resources 120 and/or the integration server 102 may send a challenge request to the clinical system resource 120, instructing the clinical system resource 120 to respond with the security token to prove the clinical system resource 120 was previously authenticated and granted rights to access the computing resources of the clinical networked computing system 100.

In some circumstances, the authentication operations, integration server 102, integration program 111, or other computing resource of the clinical networked computing system 100 may deny or revoke the access rights of the clinical system resource 120. The authentication operations may deny the access rights when the clinical system resource 120 fails to return authentication data or a security token that could successfully authenticate the clinical system resource 120. The authentication operations may (or other component of the clinical networked computing system 100) may revoke access rights previously granted to the clinical system resource 120 in response to administrator inputs from the administrator computer 152 or in response to detecting a triggering condition. Non-limiting examples of triggering conditions may include detecting changes to a current version of the clinical system resource 120 compared to the verified version in the integration database 103, receiving faulty authentication data or security token in response to an authentication challenge request, or receiving faulty licensing data in response to a license challenge request, among other triggering conditions.

Optionally, the integration program 111 performs operations for testing and certifying the interoperability of the clinical system resources 120. The integration program 111 may execute the testing operations during an onboarding or updating process, before the integration program 111 grants access privileges to the particular clinical system resource 120. In some circumstances, it may be customary practice to conclude the clinical interoperability testing on a particular (new or updated) version of a clinical system resource 120 before deploying and implementing the version control features and functions described herein within the clinical system 100. As such, the integration program 111 (or other components of the system 100) need not perform, conclude, and successfully certify the interoperability testing operations in realtime, at the time of deployment of the (new or updated) version of the clinical system resource 120. In some cases, the successful interoperability (or intraoperabilty) testing is recorded/documented and the deployment or testing may conclude at a later time using the output recorded/documented outputs stored in a non-transitory storage medium of the computing system 100. The appropriate commercial license is then updated/issued. The testing operations may implement one or more testing methods, such a test script method, data exchange test, interface testing, conformance testing, and integration testing, among other potential testing methods.

In the test script method, the integration program 111 launches script programs containing specific test scenarios that cause the clinical system resource 120 to simulate real-world scenarios using data inputs or outputs defined in the script that require the computing resources (e.g., integration program 111, clinical system resource 120, interfaces) to implement interoperability features (e.g., data format translations). The integration program 111 may monitor and evaluate the data communications between the clinical system resource 120 and other clinical system resources 120 to determine whether the clinical system resources 120 interact effectively. For instance, the script includes set of instructions that simulate various user interactions with the clinical system resource 120. The script may define, for example, the exact operations for the clinical system resource 120 (or other component of the clinical networked computing system 100) to perform, the expected responses from clinical system resource 120, and the specific data to be used by the clinical system resource 120 for the test. The integration program 111 may record the outputs produced by the clinical system resource 120 in non-transitory memory of the integration server 102 (or other device) and compares the test outputs against the expected output. The integration program 111 may identify and indicate any discrepancies between the expected and actual outcomes as a potential flaw in the interoperability functionality of the clinical system resource 120.

In an optional data exchange testing method, the integration program 111 checks if the clinical system resources 120 can exchange data accurately and seamlessly. The integration program 111 instructs the clinical system resource 120 to send data to another clinical system resource 120 (e.g., using a data API), and determines whether data is outputted or received as expected, or whether the data remains intact and unchanged according to an expected format. As an example, the integration program 111 may evaluate an output or transfer of clinical data in an XML format, from the clinical system resource 120 or the data API, follows an expected standard or format.

In an optional interface testing method, the integration program 111 instructs the clinical system resource 120 to invoke one or more interfaces. The interface testing is used to ensure that different clinical system resources 120 can communicate with each other effectively. The integration program 111 may determine, for example, whether the interface produced the correct transmission or response during communications between the clinical system resources 120. The integration program 111 evaluates, for example, the clinical system resource 120 calls to the interfaces and the outputs produced by the interactions between the clinical system resource 120 and the interfaces. The integration program 111 verifies whether the particular clinical system resource 120 is configured to effectively access and use the interfaces assigned to the clinical system resource 120 (e.g., the data API for communication and data exchange). For instance, the integration program 111 may define the test case in a script and instructs the clinical system resource 120 or interface to execute the test case. The integration program 111 may analyze the results. The integration program 111 may identify any issues in the interaction between clinical system resources 120 using the interface, such as data loss, incorrect data transmission, or issues with request and response program routines.

In an optional conformance testing method, the integration program 111 instructs the clinical system resource 120 to, for example, generate various outputs. The integration program 111 then evaluates the outputs to determine whether the clinical system resource 120 adheres to expected formats, standards, and protocols required by the clinical networked computing system 100. Other forms testing the interoperability of the clinical system resource 120 or other resources (e.g., interface programs).

The integration program 111 may determine whether the test case of a particular computing resource (e.g., interface, clinical system resource 120) failed or passed based upon comparing the actual outputs against expected outputs defined in the test script or other preconfigured data value. The integration program 111 may validate and certify the particular clinical system resource 120 or interface in response to determining that the clinical system resource 120 successfully passed the test case(s) applied by the integration program 111. Alternatively, the integration program 111 may compare the actual outputs against expected outputs to identify any discrepancies. The integration program 111 may validate and certify the clinical system resource 120 or the interface in response to determining that the amount of discrepancies satisfy an failure threshold amount of discrepancies (sometimes referred to herein as "interoperability testing thresholds"). The integration program 111 may store the current version of a successfully validated clinical system resource 120 into the integration database 103 as a verified version of the clinical system resource 120.

In some embodiments, the integration program 111 may be executed by the integration server 102 or an end-user device (e.g., administrator computer 152) to test and verify the interoperability of a new clinical system resource 120 under development. The integration program 111 may implement various testing methods, such as the testing methods described above. The integration program 111 may certify the new clinical system resource 120 as interoperable. The developer may publish the new clinical system resource 120 as new product in the marketplace. Alternatively, the developer may instruct the integration program 111 to store the current version of the new clinical system resource 120 into the integration database 103 as a certified version of the new clinical system resource 120. In this way, the developers may test and certify clinical system resource 120 products before offering the products to the public, or developers may test and certify homegrown clinical system resource 120 products before placing the products to the clinical networked computing system 100. In some implementations, the integration program 111 references metadata of a new clinical system resource 120 to confirm whether a new clinical system resource 120 was previously certified as being interoperable.

The integration program 111 or other components of the clinical networked computing system 100 (e.g., integration server 102, interface programs) may implement version control functions to govern changes to the clinical system resources 120 of the clinical networked computing system 100. The integration database 103 includes database records containing various types of versions or component information about the verified version of the clinical system resource 120. The version control functions may compare data outputs generated, or functions performed, by the clinical system resource 120 against corresponding version information of the verified version in the integration database 103.

With reference to FIG. 1B, an example embodiment includes a radiation treatment device 120*i* that receives and analyzes data inputs from treatment sensors 120*f*-120*h* for Surface Guided Radiation Therapy (SGRT). The radiation treatment device 120*i* includes a control device having a processor that adjusts a radiation beam according to sensor data received from the treatment sensors 120*f*-120*h*. The treatment sensors 120*f*-120*h* include cameras from disparate vendors that generate sensor data in the form of media image data according to disparate media data formats. The clinical system resource 120 may, for example, be a product of the same or different vendor from the vendors of the treatment sensors 120*f*-120*h* or implement the same or different data formats of the treatment sensors 120*f*-120*h*. In this way, the treatment sensors 120*f*-120*h* and the radiation treatment device 120*i* represent heterogenous clinical system resources 120.

The SGRT functions of the treatment sensors 120*f*-120*h* (e.g., cameras) are used for motion management in radiation therapy to track and capture a patient's motion during the radiation therapy. The radiation treatment device 120*i* receives measurement outputs from the treatment sensors 120*f*-120*h* and adjusts, for example, beam angle, dosage, or other parameters of the treatment. The treatment sensors 120*f*-120*h* and/or the radiation treatment device 120*i* may be products of disparate vendors with disparate data formats or functions. The radiation treatment device 120*i* may receive the data inputs from the treatment sensors 120*f*-120*h* and invoke a motion management interface (MMI) to ingest, standardize, and/or analyze the motion and position information in the input data. The MMI in radiation therapy includes software programming that helps to, for example, continuously track the position and movement of a patient's tumor or patient in real time, thereby enabling the radiation treatment device 120*i* to deliver accurate and precise radiation to the patient's tumor while minimizing the radiation exposure of healthy tissues. In the context of interoperability or other clinical functions, the MMI programming acts as a translational bridge API, allowing the different clinical system resources 120 (e.g., disparate treatment sensors 120*f*-120*h*) to, for example, access and exchange movement data. For instance, a SGRT software application controlling the radiation treatment device 120*i* may exchange data with the treatment sensors 120*f*-120*h* by calling the MMI in the integration program 111 or integration database 103.

Figure 2:
FIG. 2 shows operations of a method for onboarding and hosting a clinical system resource at a clinical computing system architecture having a plurality of on-premises computing resources of a closed computing network, according to an embodiment.

FIG. 2 shows operations of a method 200 for onboarding and hosting a clinical system resource at a clinical computing system architecture having a plurality of on-premises computing resources of a closed computing network, according to an embodiment.

Embodiments may include additional or alternative operations or omit certain operations from those of the method 200 and still fall within the description of FIG. 2. Moreover, the operations of the method 200 are described as being performed by a server of a clinical networked computing system coupled to a closed network, though embodiments are not so limited. Any number of additional or alternative computing devices of the clinical networked computing system and closed network may perform the operations of the method.

In operation 202, the server receives onboarding or access request from a clinical system resource seeking access to the closed network and computing resources (e.g., interface functions). The request seeks access to a clinical system resource.

In operation 204, the server performs an authentication operation for authenticating the clinical system resource. The server obtains authentication information associated with the clinical system resource, which may include a purported authentication credential and an authentication protocol. The server may perform the authentication operations by exchange challenge request and response messages with the authentication operations of an interface program (e.g., API) of the clinical system resource. The server authenticates the clinical system resource based upon comparing the purported authentication data against a stored expected authentication credential. granting, In operation 206, the server performs testing and verification operations for verifying the clinical system resource is an interoperable resource according to interface programs used by the clinical system resource. The server may execute the testing operations during an onboarding or updating process, before the integration program 111 grants access privileges to the particular clinical system resource 120. The testing operations may implement one or more testing methods, such a test script method, data exchange test, interface testing, conformance testing, and integration testing, among other potential testing methods. The integration program 111 may identify and indicate any discrepancies between the expected and actual outcomes as a potential flaw in the interoperability functionality of the clinical system resource 120.

The integration program may determine whether the test case of a particular computing resource (e.g., interface, clinical system resource) failed or passed based upon comparing the actual outputs against expected outputs defined in the test script or other preconfigured data value. The integration program may validate and certify the particular clinical system resource or interface in response to determining that the clinical system resource successfully passed the test case(s) applied by the integration program. Alternatively, the integration program may compare the actual outputs against expected outputs to identify any discrepancies. The integration program may validate and certify the clinical system resource 120 or the interface in response to determining that the amount of discrepancies satisfy an failure threshold amount of discrepancies. The integration program may store the current version of a successfully validated clinical system resource into the integration database as a verified version of the clinical system resource.

In operation 208, the server performs a validation operation for validating license data associated with the clinical system resource. The server sends a challenge request message to the clinical system resource, requesting license data (e.g., software key, API key). Alternatively, the server queries a database for license data. The server may receive the purported license data associated with the clinical system resource and compare the purported license data against stored expected license data. The server may validate the clinical system resource as a licensed instance or licensed component of the clinical networked computing system, based upon comparing the purported license data against stored expected license data.

In operation 210, the server grants access rights to the clinical system resource based on validating (as in operation 208), authenticating (as in operation 204), and verifying (as in operation 206) the clinical system source. In operation 212, the server stores a set of resource configurations into a database record that represents a verified version of the clinical system resource.

Optionally, in operation 214, the server revokes the access rights of the clinical system resource. The server may revoke the access rights in response to determining a new version of the clinical system resource seeking access to computing resources of the clinical networked computing system. The server might also revoke the access rights in response to determining that the clinical system resource is not valid, not authenticated, or not verified as interoperable.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A computer-implemented method for hosting resources in a computing network, comprising:

obtaining, by a computer of a computing network, authentication information associated with a clinical system resource of the computing network, the authentication information including a purported authentication credential and an authentication protocol, wherein the clinical system resource generates at least one attribute of a patient treatment;

authenticating, by the computer, the clinical system resource for generating the at least one attribute of the patient treatment based upon comparing the purported authentication credential against a stored expected authentication credential corresponding to one or more versions of the clinical system resource;

identifying, by the computer, one or more interface programs for the clinical system resource to exchange the at least one attribute of the patient treatment with a software application of a clinical therapy machine;

verifying, by the computer, the clinical system resource as an interoperable resource in response to determining that the at least one attribute of the patient treatment generated at the clinical system resource satisfies one or more interoperability testing thresholds corresponding to one or more interoperability testing operations using the one or more interface programs to exchange the at least one attribute of the patient treatment generated at the clinical system resource with the software application of the clinical therapy machine; and storing, by the computer, based on verifying the clinical system resource as an interoperable resource, a set of resource configurations into a database record representing a new instance of a verified version of the clinical system resource, the set of resource configurations including a listing of function outputs, the authentication protocol, a listing of the one or more interface programs for the clinical system resource.

2. The method according to claim 1, further comprising:

obtaining, by the computer, purported license data associated with the clinical system resource; and validating, by the computer, the clinical system resource based upon comparing the purported license data against stored expected license data.

3. The method according to claim 2, further comprising granting, by the computer, access rights to the clinical system resource for executing the one or more interface programs based upon authenticating, verifying, and validating the clinical system resource.

4. The method according to claim 3, further comprising transmitting, by the computer, a security token to the clinical system resource indicating the access rights as granted to the clinical system resource.

5. The method according to claim 1, further comprising generating, by the computer, a notification for an end-user device indicating a new version of the clinical system resource, in response to identifying a change to at least one of the listing of function outputs or the authentication protocol compared against the verified version of the clinical system resource.

6. The method according to claim 1, further comprising revoking, by the computer, access rights as granted to the clinical system resource for executing the one or more interface programs, in response to identifying a new version of the clinical system resource based upon a change to at least one of the listing of function outputs or the authentication protocol compared against the verified version of the clinical system resource.

7. The method according to claim 1, wherein the one or more interface programs include at least one of data exchange and integration application programming interface (API), a healthcare scripting API, a quality assurance (QA) API, a database access API, a Motion Management Interface (MMI), or a Varian Treatment Interface (VTI®).

8. The method according to claim 1, wherein determining that the clinical system resource satisfies the one or more interoperability testing thresholds includes:

executing, by the computer, an interoperability testing operation for an interface program to generate one or more testing outputs; and determining, by the computer, a testing discrepancy for comparison against an interoperability testing threshold, based upon comparing the one or more testing outputs against one or more expected outputs for the interoperability testing operation.

9. A system for hosting resources in a computing network, comprising:

a database of a computing network configured to store a plurality of database records for a plurality of verified versions of a plurality of clinical system resources; and a server of the computing network comprising a processor and configured to:

obtain authentication information associated with a clinical system resource of the computing network, the authentication information including a purported authentication credential and an authentication protocol, wherein the clinical system resource generates at least one attribute of a patient treatment;

authenticate the clinical system resource for generating the at least one attribute of the patient treatment based upon comparing the purported authentication credential against a stored expected authentication credential corresponding to one or more versions of the clinical system resource;

identify one or more interface programs for the clinical system resource to exchange the at least one attribute of the patient treatment with a software application of a clinical therapy machine;

verify the clinical system resource as an interoperable resource in response to determining that the at least one attribute of the patient treatment generated at the clinical system resource satisfies one or more interoperability testing thresholds corresponding to one or more interoperability testing operations using the one or more interface programs to exchange the at least one attribute of the patient treatment generated at the clinical system resource with the software application of the clinical therapy machine; and store, based on verifying the clinical system resource as an interoperable resource, a set of resource configurations into a database record of the database representing a new instance of a verified version of the clinical system resource, the set of resource configurations including a listing of function outputs, the authentication protocol, a listing of the one or more interface programs for the clinical system resource.

10. The system according to claim 9, wherein the server is further configured to:

obtain purported license data associated with the clinical system resource; and validate the clinical system resource based upon comparing the purported license data against stored expected license data.

11. The system according to claim 10, wherein the server is further configured to grant access rights to the clinical system resource for executing the one or more interface programs based upon authenticating, verifying, and validating the clinical system resource.

12. The system according to claim 11, wherein the server is further configured to transmit a security token to the clinical system resource indicating the access rights as granted to the clinical system resource.

13. The system according to claim 9, wherein the server is further configured to generate a notification for an end-user device indicating a new version of the clinical system resource, in response to identifying a change to at least one of the listing of function outputs or the authentication protocol compared against the verified version of the clinical system resource.

14. The system according to claim 9, wherein the server is further configured to revoke access rights as granted to the clinical system resource for executing the one or more interface programs in response to identifying a new version of the clinical system resource based upon a change to at least one of the listing of function outputs or the authentication protocol compared against the verified version of the clinical system resource.

15. The system according to claim 9, wherein the one or more interface programs include at least one of data exchange and integration application programming interface (API), a healthcare scripting API, a quality assurance (QA) API, a database access API, a Motion Management Interface (MMI), or a Varian Treatment Interface (VTI®).

16. The system according to claim 9, wherein, when determining that the clinical system resource satisfies the one or more interoperability testing thresholds, the server is configured to:

execute an interoperability testing operation for an interface program to generate one or more testing outputs; and determine a testing discrepancy for comparison against an interoperability testing threshold, based upon comparing the one or more testing outputs against one or more expected outputs for the interoperability testing operation.

17. A non-transitory computer-readable medium of computing network coupled to one or more processors of the computing network and containing executable instructions that, when executed by the one or more processors, causes the one or more processors to:

obtain authentication information associated with a clinical system resource of the computing network, the authentication information including a purported authentication credential and an authentication protocol, wherein the clinical system resource generates at least one attribute of a patient treatment;

authenticate the clinical system resource for generating the at least one attribute of the patient treatment based upon comparing the purported authentication credential against a stored expected authentication credential corresponding to one or more versions of the clinical system resource;

identify one or more interface programs for the clinical system resource to exchange the at least one attribute of the patient treatment with a software application of a clinical therapy machine;

verify the clinical system resource as an interoperable resource in response to determining that the at least one attribute of the patient treatment generated at the clinical system resource satisfies one or more interoperability testing thresholds corresponding to one or more interoperability testing operations using the one or more interface programs to exchange the at least one attribute of the patient treatment generated at the clinical system resource with the software application of the clinical therapy machine; and store, based on verifying the clinical system resource as an interoperable resource, a set of resource configurations into a database record of a database representing a new instance of a verified version of the clinical system resource, the set of resource configurations including a listing of function outputs, the authentication protocol, a listing of the one or more interface programs for the clinical system resource.

18. The non-transitory computer-readable medium of claim 17, wherein the executable instructions, when executed by the one or more processors, further cause the one or more processors to:

obtain purported license data associated with the clinical system resource; and validate the clinical system resource based upon comparing the purported license data against stored expected license data.

19. The non-transitory computer-readable medium of claim 17, wherein the executable instructions, when executed by the one or more processors, further cause the one or more processors to:

grant access rights to the clinical system resource for executing the one or more interface programs based upon authenticating, verifying, and validating the clinical system resource; and transmit a security token to the clinical system resource indicating the access rights as granted to the clinical system resource.

20. The non-transitory computer-readable medium of claim 17, wherein the executable instructions, when executed by the one or more processors, further cause the one or more processors to:

revoke access rights as granted to the clinical system resource for executing the one or more interface programs in response to identifying a new version of the clinical system resource based upon a change to at least one of the listing of function outputs or the authentication protocol compared against the verified version of the clinical system resource.

* * * * *